United States Patent [19]

Dardik et al.

[11] 3,988,782

[45] Nov. 2, 1976

[54] NON-ANTIGENIC, NON-THROMBOGENIC INFECTION-RESISTANT GRAFTS FROM UMBILICAL CORD VESSELS AND PROCESS FOR PREPARING AND USING SAME

[76] Inventors: Irving I. Dardik, 130 de Vriese Court, Tenafly, N.J. 07670; Herbert Dardik, 806 Washburn, Teaneck, N.J. 07666

[22] Filed: Apr. 1, 1975

[21] Appl. No.: 563,998

Related U.S. Application Data

[63] Continuation-in-part of Ser. No. 543,462, Jan. 23, 1975, which is a continuation-in-part of Ser. No. 376,948, July 6, 1973, Pat. No. 3,894,530.

[52] U.S. Cl. .............................................. 3/1; 3/1.4; 3/13; 128/1 R; 128/334 R
[51] Int. Cl.² .......................................... A61F 1/24
[58] Field of Search ............... 3/1, 1.4, 13; 128/1 R, 128/334 R, 334 C, 335, 335.5

[56] References Cited
UNITED STATES PATENTS 2,127,903  8/1938  Bowen .................................. 3/1.4
3,562,820  2/1971  Braun ................................... 3/1.4

OTHER PUBLICATIONS

"The Use of Umbilical Cord for Reconstruction of Abdominal Wall defects," by Frederick C. Heaton et al., Surgical Forum, vol. 21, 1970, pp. 56–57.

Primary Examiner—Ronald L. Frinks
Attorney, Agent, or Firm—Blum, Moscovitz, Friedman & Kaplan

[57] ABSTRACT

Arteries and veins of umbilical cords are hardened and shaped by processes described. Prostheses in the form of tubes, patches and conduits are prepared from the shaped vessels. The prostheses are used as reinforcements and replacements for vessels, ducts, intestines and urinary bladders. The processes result in products which have vanishingly low antigenicity and thrombogenicity, are resistant to infection and which may be stored indefinitely for use when needed by a surgeon.

55 Claims, 8 Drawing Figures

NON-ANTIGENIC, NON-THROMBOGENIC INFECTION-RESISTANT GRAFTS FROM UMBILICAL CORD VESSELS AND PROCESS FOR PREPARING AND USING SAME

CROSS-REFERENCE TO RELATED APPLICATION

The present application is a Continuation-In-Part application of Ser. No. 543,462, filed Jan. 23, 1975, itself a Continuation-In-Part application of Ser. No. 376,948 filed July 6, 1973, now U.S. Pat. No. 3,894,530.

BACKGROUND OF THE INVENTION

With the improvement in diagnostic techniques as well as surgical techniques, the need for flexible materials which may be implanted in the body has grown rapidly. Thus, vascular prostheses are needed for replacement of diseased or traumatized vessels including aneurysms, patches are needed for covering relatively large openings in intestines or other organs such as may be caused by bullet wounds, patches are needed for reinforcing defective sections of intestines or esophagus and coverings are needed for implanted organs such as heart valves and pacemakers. A particularly pertinent example arises in the repair of detached retinas. At the present time, so-called eye-slings are fashioned from silicone plastic or fascia lata. In the procedure, the sling is sewn to the eyeball in such a fashion that it compresses the eyeball, the compression generally being such as to increase the internal pressure by some 30 mm of Hg. However, these materials may erode the eye or lead to infection since they are foreign bodies. Also, the use of facia lata involves a second operation since this material must be taken from the patient.

Considerable success has been achieved in the use of synthetic vascular grafts for replacement of defective arteries and veins. However, admirable as have been the results achieved with such synthetic materials, they have severe limitations. There is a substantial failure rate due to infection supervening and there may be biologic failure or degradation by fibrin layering, intimal or sub-intimal hyperplasia, and aneurysm formation. Perhaps the most important of the limitations is that grafts smaller than about 5 mm in inside diameter almost invariably become blocked by clots which form therein and clotting difficulties arise in certain bodily locations even with vascular grafts having inside diameters as great as 10 mm. Moreover, a delicate balance must be struck in the porosity of the synthetic graft since the wall thereof must be sufficiently porous to permit ingrowth and deposition of fibrin so that eventually the wall is covered with scar tissue both internally and externally and yet not be so porous that hemorrhage occurs. This makes it necessary to pre-clot the graft prior to use.

Such grafts are made, in general, either of polyester (Dacron) and Teflon. Fabrics woven or knitted of these polymers have also been useful as patches or reinforcements. However, the range of usefulness is restricted. As is obvious, the necessity for pre-clotting is a substantial disadvantage as is the fact that they occasionally cause inflammation. As aforenoted, a major disadvantage is the fact that they cannot reliably be used in the form of vessels having an inside diameter smaller than 5 mm. This precludes the possibility of replacement of coronary vessels as well as the minute vessels in fingers. Also, they do not give full reinforcement until they are completely overgrown with scar tissue.

Arterial homografts (human arteries) were used to restore continuity but limited supply, limited range of sizes and development of aneurysms and arterial sclerosis necessitated the search for better substitutes. In view of the difficulties encountered with the various types of artificially constructed grafts, these difficulties including: (1) infection which may lead to hemorrhage, sepsis and death; (2) thrombogenicity of the inner lining of the graft so that the graft is predisposed to clotting which may result in total occlusion of the graft and distal embolism of the clot; (3) the rigidity of fabric grafts which may result in twisting and kinking especially where a joint is crossed such twisting and kinking leading to graft occlusion, these must be considered as having serious deficiencies.

In the attempt to avoid artificial grafts, a variety of new techniques have been developed. These include "cleaning out" an artery such as by carbodissection, dilating arteries, development of bovine heterografts, and creating collagen tubes by inserting a mandrel within the recipient for later use of a graft.

It is known that homografts have been used for vascular grafting with considerable success. Commonly, the saphenous vein has been used in cases where the patient is the donor (an autograft) and where another human is a donor (allograft). These vessels require no treatment before implantation; however, they present problems of unavailability, disparity in size, nonuniform caliber, presence of valves and varicies, and the need for additional authorization in the case of allografts. The removal of the saphenous vein to be used for vascular grafting in the same patient involves keeping the patient on the table for a substantially longer time. Moreover, the operation is quite delicate and frequently is a failure. Finally, where rejection is a problem and the patient needs further grafting after the patient's own saphenous veins have been removed, repair by this method becomes impossible.

For these reasons as well as others which will appear it would be highly desirable to provide a new material for use as replacement and reinforcement for vessels and other organs of the body which would be free of the problems of clotting, thrombogenicity and antigenicity. Moreover, as will be disclosed herein, the new material proposed as a source for repair and replacement of vessels and other organs of the body can be prepared in a variety of forms which will give rise to new techniques of great usefulness.

SUMMARY OF THE INVENTION

Umbilical cords contain both primitive veins and arteries. Surprisingly, these veins and arteries have vanishingly low antigenicity and thrombogenicity when hardened as disclosed herein, properties which are extremely desirable in a material to be used for implantation into patients. The steps involved in preparing such veins and arteries for use in implantation are exemplified by the processing of the human umbilical cord which contains one vein and two arteries. However, the umbilical cords of other mammals can be similarly treated and used.

A mandrel is passed through the vein to straighten the cord and serve as a support during the subsequent dissection of the arteries and extraneous tissue therefrom. The mandrel is removed and the vein is flushed clean of residual blood. The arteries may also be flushed. If start of the chemical treatment is to be postponed for longer than 1–2 hours, the vessels may be refrigerated at about 4° C for up to several weeks or freeze dried. If the dissection is to be postponed after recovery of the umbilical cord it may also be stored under refrigeration.

The vessels are irrigated for several minutes with an aldehyde solution after which they may also be placed on mandrels. Each vessel is placed in a hardening solution on its mandrel, the hardening solution also containing an aldehyde. The vessel shrinks down onto the mandrel taking the shape of the mandrel. Glutaraldehyde and dialdehyde starch are effective as hardening agents as are formaldehyde and glyoxal. However, glutaraldehyde is preferred.

It is desirable that the vessel be treated at this point to remove residual aldehyde. In addition to conventional rinsing, the vessel may be treated with a reagent which reacts with aldehyde, suitable reagents being amino-acids, salts thereof, hydroxylamine, peroxides, peracids and hypochlorites. The preferred reagent is sodium L-glutamate. The vessel can then be removed from the mandrel, treated to remove residual hardener and stored in a dilute aldehyde solution in preparation for use.

In preparation for implantation, the selected vessel is rinsed with a sterile liquid such as water, saline etc. Any residual aldehyde on the vessel is preferably removed prior to use. This can be effected by use of the reagents described above. The pH of the reagents should be adjusted to about 7.5 to 8.5. The adjustment can be made conveniently with $NaHCO_3$ or a phosphate buffer.

A mandrel inserted in a vein or an artery can be used for shaping either type of vessel and simultaneously eliminating the valves of Hoboken from the arteries. Alternatively, the vein or artery can be placed inside a mold, conveniently of aluminum, and distended by the use of a pressurized fluid until the vessel takes the shape of the interior of the mold. A hardening solution is used to fix the vessel in the shape either of the mandrel or of the mold. The product, although hardened, is sufficiently flexible so that it can be slit and laid out flat and cut into segments. In this way, sections can be used as strips or as patches for a variety of purposes. Also, by controlling the degree of hardening the material can be shaped on a lathe to give a product of uniform wall thickness.

Dropping the temperature of a vessel increases its rigidity. In fact, it may be frozen as a means of preserving it during storage. Using the term "frozen" to indicate a drop in temperature sufficient to render the vessel stiff enough for shaping on a lathe, the cord with a mandrel through the vein can be mounted in a lathe and then rotated so that all elements other than the vein can be cut away quickly. This facilitates obtaining the vein when it is only the vein which is desired this being generally due to the fact that it is greater in diameter than are the arteries.

The Wharton's jelly which is one of the constituents of the cord can be partially removed from the cord prior to dissection thereof by soaking the cord in a solution of hyaluronidase.

A stiffer product can be obtained by soaking the vessels in alcohol prior to treating with a hardening agent.

In general, the vessels will not be used in exactly the form resulting from treatment of the umbilical cord described above. Usually, it will be necessary to trim the vessel to a shorter length, or to slit it, open it up so that it can be made to lie flat and then cut to length so that it can be used as a patch. The term "segments" will henceforth be used to indicate entire vessels, portions of vessels, vessels in tubular form or patches taken from vessels.

Segments may be used for replacement of non-pulsatile tubular members in the body such as bile ducts and ureters. Other uses are as a retinal eye sling, a patch for reinforcement of a section of the intestine, a skin graft, a reinforcement for an artery or a vein, a patch to bridge defect or to augment a portion of a urinary bladder and to create an artificial conduit between the bladder and the skin. Strips formed by slitting a vein or artery and opening same up, can be used for covering the join between two sections of a bowel or a vein or an artery, such a join being an anastamosis. A patch can also be used to cover a gash which has been sewn together. It will reinforce the join and prevent leaks and other disruptions. It can also be used on the esophagus.

Accordingly, an object of the present invention is a method of hardening vessels from umbilical cords, segments of which are to be used as implants in or grafts on patients.

Another object of the present invention is a method of shaping vessels from umbilical cords.

A further object of the present invention is a method of preparing segments of umbilical cords which are non-antigenic and non-thrombogenic.

An important object of the present invention is the provision of umbilical cord segments which may be stored in preparation for surgical use.

Another important object of the present invention is the provision of umbilical cord segments which may be used as eye slings and as skin grafts.

A significant object of the present invention is a group of surgical procedures using umbilical cord segments prepared in accordance with the present invention.

A particularly important object of the present invention is the use of umbilical cord segments for reinforcement of members joined by anastamosis.

Still other objects and advantages of the invention will in part be obvious and will in part be apparent from the specification.

The invention accordingly comprises the several steps and the relation of one or more of such steps with respect to each of the others, and the article possessing the features, properties, and the relation of elements, which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

The vessels in umbilical cords of mammals and especially of humans when considered for use in repair, reconstruction, replacement, reinforcement and augmentation of vessels, organs and other members, both interior and exterior of the body, are unique with respect to both origin and morphology. Taking the human umbilical cord as representative, though it is to be understood that the umbilical cords of all mammals may be used in the fashions described herein, it is composed of a vein and two arteries surrounded by a sticky jelly-like substance called Wharton's jelly, all encased in the surrounding tissue. The umbilical cord may vary in length from a few inches to over 3 feet in length and is highly flexible. Both the arteries and the veins contained in the cord are suitable for use in surgery as will be described.

Since hardened and shaped segments are superior to the untreated umbilical cord vessels for use in surgical implantation, it is obviously of great advantage to be able to have a supply of umbilical cord vessels in various configurations ready for use as the physician requires. The freshly dissected vessels can be stored after freeze-drying or under refrigeration for limited periods; however, it is preferable that they be chemically treated so that storage for indefinite periods becomes possible even when facilities for refrigeration are lacking. In our copending Application Ser. No. 543,462 filed Jan. 23, 1975, methods of treating the umbilical cord chemically have been disclosed. However, the previous application was directed primarily toward the use of umbilical cord vessels in vascular surgery, such use requiring that the umbilical cord vessels withstand pulsatile pressures. Synthetic mesh reinforcement of the cord vessels was disclosed. The present invention is directed toward a wider spectrum of uses in which the strength requirements are less severe. For convenience, as aforenoted, the term "segments" will be used to designate portions of cord vessels or entire cord vessels in a variety of shapes and forms other than that in which it occurs in nature. Included will be vessels in tubular form where the tubular form may be tapered or essentially rectangular in cross-section, and portions of vessels which have been slit so that they can be laid out flat.

Figure 1:
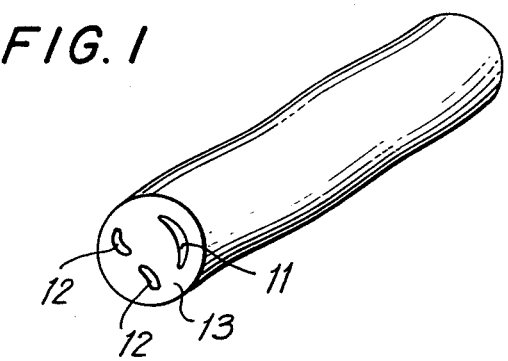
FIG. 1 is a view in perspective of an umbilical cord prior to treatment.

A human umbilical cord is shown in FIG. 1, the cord containing through the length thereof a vein 11, two arteries 12 and the aforementioned Wharton's jelly 13. The first step in the preparation of vein segments in accordance with the present invention is to pass a mandrel through the vein. The arteries and excess tissue are dissected away from the vein. The mandrel is removed and the vein is then flushed clean of residual blood, using any of water, a dilute solution of hydrogen peroxide, Ringer's lactate solution or sterile saline solution, Ringer's lactate solution being preferred.

Since the cord is very flexible and, in fact, may be twisted as well, passing the mandrel through the vein straightens out the cord and makes it convenient to handle. The mandrel may be mounted for rotation in a suitable fixture. The arteries are twisted and coiled around the vein and dissection of the arteries from the cord is therefore a delicate task which is facilitated by the use of the mandrel in the vein and mounting for rotation.

Variations in this procedure are possible. Where only the vein is desired, the cord, mounted on the mandrel, may be frozen after which the mandrel can be chucked in a lathe and all material other than the vein itself cut away using an appropriate cutting tool. Furthermore, if desired, the vein itself may be trimmed to constant thickness.

Another mode of handling the cord is to soak it in hyaluronidase solution to reduce the content of Wharton's jelly prior to the dissection step.

After dissecting out the desired vessel or vessels and clearing of residual blood, they are irrigated for several minutes with a hardening agent, preferably 3 - 10 minutes. This step effects partial elimination of Hoboken's valves from the arteries. The hardening agent found most suitable is the class of aldehydes. Examples are formaldehyde, glyoxal, dialdehyde starch and glutaraldehyde, with glutaraldehyde being the best from the standpoints of elimination of any traces of antigenicity and thrombogenicity and convenience, with a solution of dialdehyde starch being next best. The concentration of the glutaraldehyde solution should be between about 0.15% and 0.7%. The concentration of dialdehyde starch should be between about 0.5 to 2.0% by weight. At lower concentrations the glutaraldehyde solution does not render the material non-antigenic, while at higher concentrations the reaction is too rapid and embrittles the wall of the vessel.

After irrigating a vessel with a hardening solution, the vessel is slipped onto a mandrel of appropriate shape. The vessel on the mandrel is then placed in a tank (not shown) of hardening solution for about 15 to 45 minutes, during which time the vessel conforms to the shape of the mandrel. A preferred solution for hardening the vessel is 0.5% glutaraldehyde buffered with 1% sodium bicarbonate so that the pH of the solution is between 7.5 and 8.5. The hardening agent causes the vessel to conform to the shape of the mandrel and also increases the strength of the vessel material. A vein 11 is shown on a cylindrical mandrel 15 in FIG. 2.

Figure 3:
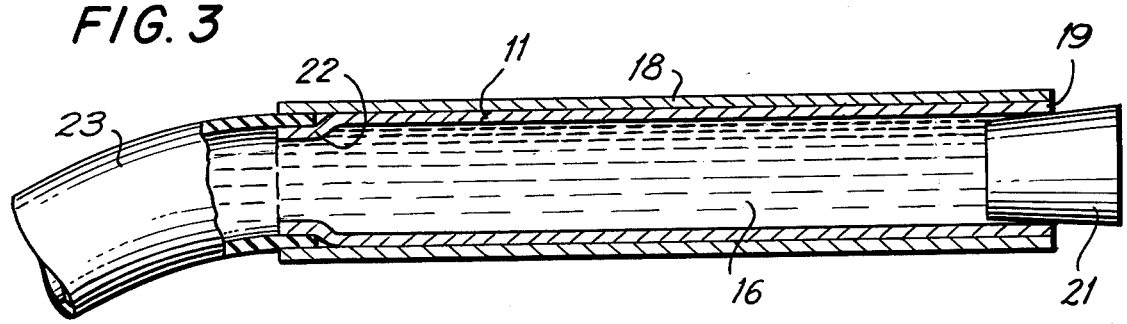
FIG. 3 is a view in partial section of an umbilical cord vessel pressed against the interior of a mold hydraulically.

Another means of shaping a vessel is shown in FIG. 3 in which a vein 11 is inserted in a tubular mold 18, end 19 of vein 11 being closed with stopper 21. The other end 22 of vein 11 is connected to hose 23 for introduction of hardening solution 16 under moderate pressure. The pressure of the hardening solution 16 forces vein 11 against the interior of mold 18 to conform to said interior. This process results in a vessel having a smoothed exterior.

Figure 2:
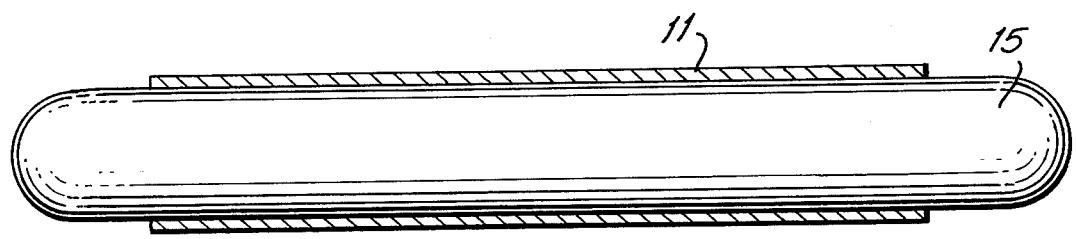
FIG. 2 is a sectional view of an umbilical cord vessel on a cylindrical mandrel.
Figure 4:
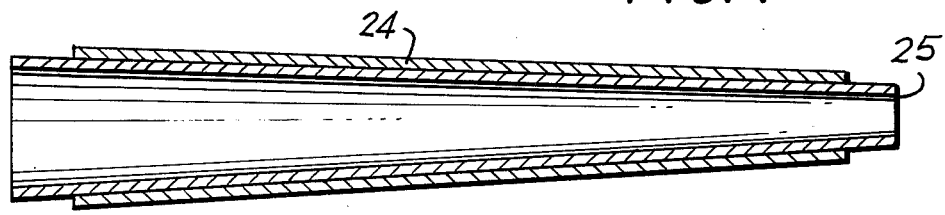
FIG. 4 is a sectional view of an umbilical cord vessel on a tapered mandrel.

The practice of shrinking a vein or artery onto a cylindrical mandrel 15 as in FIG. 2 or a tapered mandrel 25 as in FIG. 4 has the advantage that any internal irregularities such as the valves of Hoboken are eliminated, the reference numeral 24 indicating a vessel segment where the vessel may be either a vein or an artery.

The vein in the human umbilical cord is substantially larger than the arteries. Consequently, where larger segments are desired, veins are used in preference to arteries. Using either an internal mandrel or an external mold, a vein can be distended out to about 1.0 cm internal diameter. The diameter of a human umbilical cord artery can be distended up to about 5 mm and can be collapsed down to about 0.5 mm. Arteries of such small diameter are particularly valuable for replacement of blood vessels in the body. In this context, the umbilical cords of the larger mammals, while not so readily available as those of humans, contain larger vessels so that larger and thicker-walled vessels and patches become available through use of vessels from such sources. Also, the small mammals provide vessels of smaller diameter, such vessels being needed for specialized applications such as in fingers and toes.

It should be noted that for use of segments treated in accordance with the present invention in pulsatile blood vessels smaller than about 2 mm internal diameter, reinforcement with artificial mesh is unnecessary. This follows not only from the fact that tubes of smaller diameter can withstand higher pressure, in general, but from the fact that in collapsing the vessels, the wall thickness is increased. Soaking the vessel in alcohol prior to the aldehyde treatment results in a stiffer vessel.

After hardening the vessel, it is rinsed to remove most of the hardener. A 1% solution of $NaHCO_3$ may be used. It is then desirable to treat the vessel or segment for a period of 30 – 45 minutes with a reagent which reacts with residual aldehyde. Suitable materials are amino acids, alkali salts thereof and oxidizing agents in dilute form such as peroxides, peracids and hypochlorites. The amino acids as sodium salts, and preferably of L-sodium glutamate, L-sodium alanine, L-sodium phenylalanine and L-cysteine are particularly suitable for this purpose because they are antithrombogenic, the best of the above being the glutamate. The mechanism is believed to depend on condensation of the amine group of the aminoacid with the carbonyl group of aldehydes. This leaves the carboxyl group of the condensate free to ionize and impart a negative charge to the surface of the vessel. Negatively charged surfaces are known to be antithrombogenic.

Although the preferred method of storage subsequent to hardening and shaping of the vessel is a dilute solution of aldehyde, it is advantageous to treat the vessel with an amino acid after hardening to eliminate aldehyde as indicated. Although not known for certain, it appears the the residual aldehyde groups are initially oriented so that they are readily accessible for reaction with an amine group, whereas, after storage unreacted aldehyde groups are oriented inwardly of the vessel or segment wall and so inaccessible.

The preferred method of storage of segments is in a dilute solution of aldehyde, 0.5% glutaraldehyde being preferred. Some further hardening of the segment takes place over a period of 4–6 days. However, the extent of hardening during storage is small and can readily be compensated for in the principal hardening stage.

In preparation for implantation, after storage, the segment is rinsed, as in sterile saline or 1% $NaHCO_3$ solution. It is preferably treated again with sodium L-glutamate or one of the other aforenoted compounds to eliminate residual aldehyde.

An alternate method of storage is in a solution of 40–50% aqueous alcohol containing about 1% of alcohol. Treatment of segments stored by this method with reagent to remove aldehyde is, of course, unnecessary.

As will be recognized, a substantial number of variations on the procedures outlines above are feasible. Thus, after flushing out the vein in the umbilical cord, a mandrel, either tapered or straight, may be inserted into the vein, the cord frozen, the mandrel placed in a chuck and all elements other than the vein cut away on a lathe. In the process, the exterior of the vein may be cut so that the wall thickness becomes uniform or, tapered, if so desired. As would be expected, the vessel or segment must be rendered sterile after subjection to such manipulation. Conventional non-destructive techniques such as radiation, antibiotics and elevated temperature are used.

Figure 5:
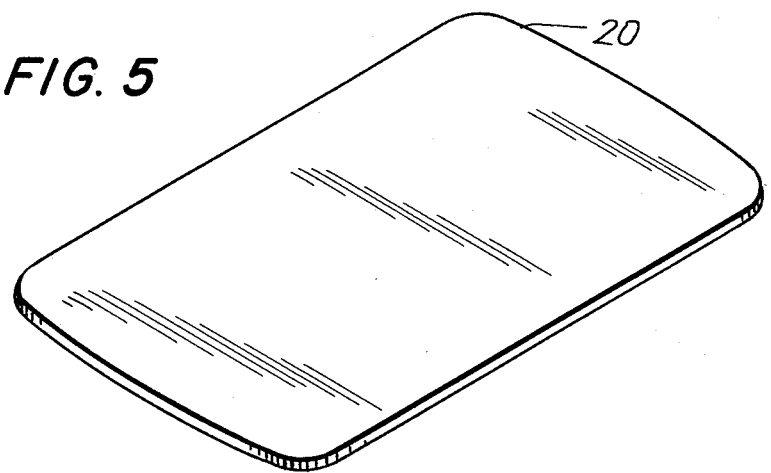
FIG. 5 is a view in perspective of a segment of an umbilical cord.
Figure 6:
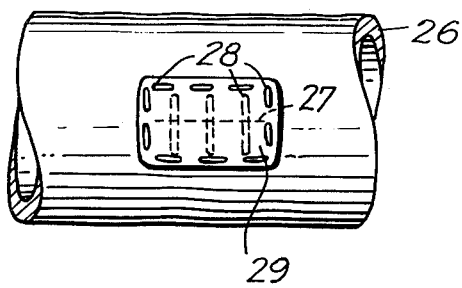
FIG. 6 is a side view of a vessel reinforced at a seam by a segment in the shape of a patch.

Another variation is to slit the vein open and lay it out flat. The use of a flat mandrel facilitates the formation of flat segments. The vessel may then be cut into segments 20 of any desired size as shown in FIG. 5, such segments to be used as reinforcements or patches. One use of such a patch is shown in FIG. 6 wherein a vessel 26, which may be a portion of a bowel which has been sewn together to form a seam 27, using sutures 28. This repair of the vessel 26 can be reinforced by placing a segment 29 as a patch over seam 27 and suturing the patch over vessel 26.

The function of such a patch is greater than mere reinforcement. As is well known, in stitching together portions of walls of organs in the body, it is necessary that the sutures not be pulled too tight and that the stitches not be too close, else the blood supply to the wall of the organ may be cut off in which case gangrene may supervene. As a result, using standard techniques, there may be leakage through the suture line in the wall. It is for this reason that drains are so commonly used. Reinforcing the seam with a patch as shown in FIG. 6, greatly decreases if not completely eliminates this danger.

Figure 7:
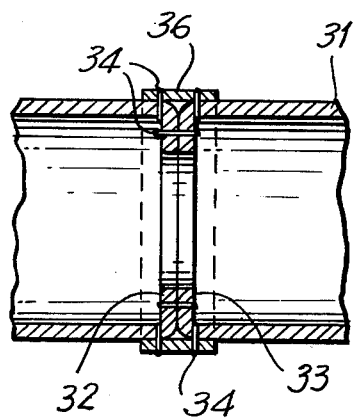
FIG. 7 is a sectional view of an anastamosis reinforced by a segment in the form of a strip.

Another version of the use of a segment prepared in accordance with the present invention is shown in FIG. 7 which represents an anastamosis in a bowel 31. In accordance with the usual surgical procedure, the two ends 32 and 33 of bowel 31 are turned inward and the ends are then sewn together with suture 34. A segment 36 is then sewn around the join between bowel ends 32 and 33, thereby eliminating or greatly reducing the danger of seepage of bowel contents into the abdomen. Needless to say, although FIG. 7 shows only a single turn of segment about the bowel, two or more turns about the bowel could also be taken.

The interiors of the vessels are somewhat rougher than the exteriors thereof, even after shaping on a mandrel. This difference persists when the vessel is opened up for forming a patch. The surgeon using such a patch can use either face at his discretion for joining to an organ.

A plurality of segments may be used in certain applications such as for lining the pericardium of the heart, or a heart valve, or for covering an artificial implant such as a pacemaker. Segments may also be used in plastic surgery as an inert reconstructive material.

Although the tensile strength of a hardened vessel is only moderate, it has other characteristics which make it highly desirable for use surgically. These are the aforenoted non-antigenicity and non-thrombogenicity as well as characteristic flexibility, slipperyness and complete compatibility with body organs and vessels.

Figure 8:
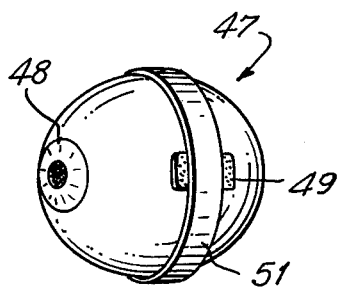
FIG. 8 is a view in perspective of an eyeball wherein the region of attachment of a retina to the interior of an eyeball is reinforced by an eye sling, the sling being formed of an umbilical cord vessel in accordance with the present invention.

There is a wide variety of surgical procedures in which cord segments can be used to great advantage. It has already been mentioned that a segment can be used to reinforce a seam and an anastamosis. It can also be used to reinforce a weak portion or a defect in the wall of an organ such as an urinary bladder. A segment can be shaped to form an artificial conduit between the urinary bladder and the skin. A most important use is as a retinal eye sling. The need for a sling arises in the surgical procedure for repairing a detached retina. The way in which an eye sling is used is shown in FIG. 8 wherein the reference numeral 47 generally indicates an eyeball. The pupil 48 of the eyeball 47 is shown and the area where a repair has been effected surgically is shown at 49. The region of repair must be held under pressure until the retina attaches itself permanently to the eyeball. For this purpose a sling 51 is wrapped around the eyeball so that the eyeball is compressed against the retina in the interior thereof. This generally requires that the internal pressure in the eyeball be increased by about 30 mm of mercury.

Up to the present time retinal eye slings have been made of silicone plastic or fascia lata. The former can erode the eyeball and precipitate infection. Consequently, a certain fraction of such procedures fail and, in such cases, blindness can result. Use of fascia lata, on the other hand, necessitates a prior operation in order to obtain the material. Substitution of a segment prepared in accordance with the present invention eliminates these difficulties. The material is completely compatible with the body and has no tendency to erode the eyeball.

Another important use for patches derived from umbilical cord vessels is in connection with skin grafting. A patch can be placed in position over a burned or traumatized area, even in the presence of infection. In many cases even a dressing is not needed. The patch "takes" quickly. Healing, including clearing of underlying infection, proceeds rapidly under the patch and with no need for the usual change of surgical dressings. The patch sloughs off when healing is sufficiently advanced. Of major importance, these grafts will persist for several months while healing proceeds.

The use of umbilical cord vessels, whether from humans or from other mammals, as can be seen from the above, presents numerous advantages. The supply is virtually unlimited and the treatment needed for rendering the vessels appropriate for use in surgery is simple. Also, many variations are possible in order to meet specific and varied needs. As a result, sterile cord vessel segments can be produced in unlimited supply and at relatively low cost. They can be stored indefinitely and in a variety of shapes and thicknesses to meet virtually any need. Assuming they are stored in dilute glutaraldehyde solution, they need only be rinsed in sterile water or saline solution or dilute $NaHCO_3$ preparatory to use. If desired, they can be further rinsed in sodium-L-glutamate to eliminate any residual aldehyde.

It has already been noted that a number of useful variations in the chemical treatment of umbilical cord vessels, i.e., segments, are possible. The following variations are based on the fact that although the major hardening of the vessel in a hardening solution takes place in a period of up to about 45 minutes, further hardening continues for 4-6 days at room temperature when the vessel is stored in a solution of a hardening agent. These variations may be categorized as follows:

1. Continue the initial hardening process for 4-6 days without interruption for elimination of aldehyde.
 1a. Keep the mandrel or mold in contact with the vessel for up to about 45 minutes.
 1b. Keep the mandrel or mold in contact with the vessel for 4-6 days.
2. Raise the temperature of the hardening solution by up to about 60° C and shorten the time of contact of the vessel with the hardening solution correspondingly, the time of contact between solution and vessel to be long enough for completion of the hardening process.
 2a. Keep the mandrel or mold in contact with the vessel only until shaping is complete.
 2b. Keep the mandrel or mold in contact with the vessel until hardening is complete.
3. Treat the hardened vessel or segment with an aldehyde-destroying reagent for a period long enough to insure essentially complete elimination of carbonyl groups from the vessel or segment.
 3a. Carry out said treatment prior to storage and sterilize by conventional means and store.
  3a.1. Carry out said treatment at ambient temperature.
  3a.2. Carry out said treatment at elevated temperature.
 3b. Carry out said treatment subsequent to storage and sterilize by conventional means.
  3b.1. Carry out said treatment at ambient temperature.
  3b.2. Carry out said treatment at elevated temperature.

It will thus be seen that the objects set forth above, among those made apparent from the preceding description, are efficiently attained and, since certain changes may be made in carrying out the above process and in the article set forth without departing from the spirit and scope of the invention, it is intended that all matter contained in the above description and shown in the accompanying drawings shall be interpreted as illustrative and not in a limiting sense.

It is also too be understood that the following claims are intended to cover all of the generic and specific features of the invention herein described, and all statements of the scope of the invention which, as a matter of language, might be said to fall therebetween.

What is claimed is:
1. A flexible, hardened segment of a mammalian umbilical cord vessel in a shape other than that in which it occurs in nature, for use as a prosthesis in mammals, said segment having vanishingly low antigenicity and thrombogenicity.
2. The segment as defined in claim 1 wherein said segment is a portion of a vein.
3. The segment as defined in claim 1 wherein said segment is a portion of an artery.
4. The segment as defined in claim 1 wherein said segment is sterile.
5. The segment as defined in claim 1 wherein said segment has a shape such that it can be manipulated into essentially planar form without wrinkling.
6. The segment as defined in claim 1 wherein said segment is tubular in form.
7. The segment as defined in claim 6 wherein said tubular segment is free of the valves of Hoboken.
8. The segment as defined in claim 1 wherein the thickness dimension of said segment is essentially uniform.

9. The segment as defined in claim 1, wherein said mammalian umbilical cord is a human umbilical cord.

10. A process for preparing a prosthesis for use in surgery comprising the steps of
   a. separating and removing at least one of the principal blood vessels from a mammalian umbilical cord;
   b. hardening said blood vessel by means of a reagent;
   c. shaping said vessel.

11. The process as defined in claim 10 further comprising the step of passing a cleansing liquid through said vessel to remove blood therefrom.

12. The process as defined in claim 11, wherein said cleansing liquid is selected from the group consisting of hydrogen peroxide, Ringer's lactate solution, sterile saline solution and water.

13. The process as defined in claim 10 wherein the separation of said vessel from said umbilical cord is carried out mechanically.

14. The process as defined in claim 10 wherein a mandrel is inserted into said vessel as a means of shaping same.

15. The process as defined in claim 10 wherein said vessel is shaped subsequent to removal of same from said umbilical cord and said shaping step comprises the substeps of inserting said vessel in an essentially tubular mold, distending said vessel against the wall of said tubular mold, and hardening said vessel so that it retains the shape of said tubular mold.

16. The process as defined in claim 10, wherein said shaping is carried out by hardening said vessel while mounted on a mandrel inserted therein.

17. The process as defined in claim 16 wherein said mandrel has an axis and is of circular cross-section throughout, and further comprising the steps of mounting said mandrel in a rotatable chuck, the axis of said chuck coinciding with the axis of said mandrel, rotating said chuck and said mandrel, and applying a cutting tool against the exterior of said vessel to shape the exterior thereof.

18. The process as defined in claim 10 wherein said vessel is shaped by hardening same while on a mandrel, and further comprising the steps of mounting said mandrel in a chuck for rotation, and cutting away the remainder of said umbilical cord by means of a cutting tool while rotating said vessel on said mandrel.

19. The process as defined in claim 10 wherein said vessel is mounted on a mandrel prior to hardening, and further comprising the steps of freezing said umbilical cord including said vessel on said mandrel, mounting said mandrel in a rotatable chuck and removing the remainder of said umbilical cord from said vessel by means of a cutting tool while rotating said mandrel.

20. The process as defined in claim 10, wherein said hardening is effected by bringing said vessel in contact with a solution of an aldehyde.

21. The process as defined in claim 20, wherein said aldehyde is selected from the group consisting of glutaraldehyde, dialdehyde starch, glyoxal and formaldehyde.

22. The process as defined in claim 20, wherein said vessel is hardened by bringing same in contact with a solution of glutaraldehyde at a concentration of from 0.15% to 0.6% by weight for a period of about 15 to about 45 minutes.

23. The process as defined in claim 20 wherein said vessel is hardened by bringing same in contact with a solution of dialdehyde starch at a concentration between about 0.5 and 2.0% by weight.

24. The process as defined in claim 10, further comprising the step of slitting said hardened vessel axially so that said vessel may be manipulated into essentially flat shape, and, optionally, cut into segments.

25. The process as defined in claim 20, further comprising the steps of washing the aldehyde-treated vessel with water, normal saline or dilute sodium bicarbonate to remove aldehyde, and then with a suitable reagent for the purpose of eliminating residual aldehyde.

26. The process as defined in claim 25 wherein said reagent is selected from the group consisting of amino acids, alkali salts of aminoacids, amines, hydroxylamines, peracids, peroxides and alkali hydrochlorite.

27. The process as defined in claim 25 wherein said reagent is an alkali salt of L-glutamic acid.

28. The process as defined in claim 10 further comprising the step of soaking said vessel in ethanol prior to hardening same, the purpose being to produce a stiffer product.

29. The process as defined in claim 10, further comprising the step of soaking said umbilical cord in a solution of hyaluronidase prior to shaping said vessel, the purpose being removal of a portion of the Wharton's jelly from said cord, and thereby to facilitate separation of said vessel from said cord.

30. The process as defined in claim 10, further comprising the step of storing said shaped vessel in a member selected from the group consisting of a dilute solution of aldehyde and a 40–50% aqueous alcohol solution containing 1% by weight of propylene oxide, in preparation for use of said shaped vessel in a surgical procedure.

31. The process as defined in claim 30, wherein said aldehyde solution is a dilute glutaraldehyde solution.

32. The process as defined in claim 10, wherein said umbilical cord is that of a human.

33. The process as defined in claim 10, wherein said shaped vessel has a form such that it is manually deformable into an essentially flat strip, and further comprising the step of binding a suitably-sized strip of said vessel about an eye as part of a surgical procedure for holding a detached retina against the inner wall of the eyeball, the strip being fastened about the eyeball so as to compress it sufficiently to generate a selected internal pressure above atmospheric.

34. The process as defined in claim 10, wherein a suitably shaped segment of said vessel is surgically attached to the interior of the pericardium of the heart to form a lining thereof.

35. The process as defined in claim 10, wherein said shaped vessel is cut to form a segment suitably shaped for use as a patch over an opening in a bowel.

36. The process as defined in claim 16, wherein said vessel is cut to form a patch for use as a reinforcement over a gap in a bowel, vessel or other organ which has been sewn together and said patch is so used.

37. The process as defined in claim 10, wherein said shaped vessel is cut into a strip and said strip is sewn over an anastamosis as a reinforcement and to prevent leakage therethrough.

38. The process as defined in claim 10, wherein said shaped vessel is used as a replacement for at least a part of an artery, a vein, a bile duct or a ureter.

39. The process as defined in claim 10, wherein said shaped vessel is used to form an artificial conduit between the bladder and the exterior of a patient.

40. The process as defined in claim 10 wherein said vessel is used as a patch to bridge or reinforce a defect in a urinary bladder.

41. The process as defined in claim 10, wherein said shaped vessel is used for surgical repair of an esophagus.

42. The process as defined in claim 10, wherein said shaped vessel is used as a patch over a surface trauma.

43. The process as defined in claim 42 wherein said trauma is a burn.

44. The process as defined in claim 42, wherein said trauma is a wound.

45. The process as defined in claim 42, wherein said trauma is infected.

46. The process as defined in claim 10, wherein said shaped vessel is used as filler material in plastic surgery.

47. The process as defined in claim 10, wherein said vessel is a vein.

48. The process as defined in claim 10, wherein said vessel is an artery.

49. The process as defined in claim 10, wherein said mammal is a human.

50. The process as defined in claim 10, wherein said shaped vessel is used as a covering for artificial, implanted organs and parts thereof.

51. The process as defined in claim 50, wherein said organ is a heart valve.

52. The process as defined in claim 50, wherein said organ is a pacemaker.

53. The process as defined in claim 10, wherein said hardening process is carried out at elevated temperature to accelerate said process.

54. The process as defined in claim 10, further comprising the step of treating said vessel with a solution for essentially eliminating any residual carbonyl groups, said step being carried out at elevated temperature.

55. The process as defined in claim 10, wherein said vessel is treated with said reagent for up to 6 days and further comprising treating said vessel with a reactant for essentially eliminating all of said reagent from said vessel.

* * * * *